United States Patent
Feuerlein et al.

(10) Patent No.: US 9,480,443 B2
(45) Date of Patent: Nov. 1, 2016

(54) METHOD FOR SELECTING A RADIATION FORM FILTER AND X-RAY IMAGING SYSTEM

(71) Applicant: Siemens Aktiengesellschaft, Munich (DE)

(72) Inventors: Ute Feuerlein, Erlangen (DE); Christiane Koch, Eggolsheim (DE); Rainer Raupach, Heroldsbach (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 2 days.

(21) Appl. No.: 14/616,775

(22) Filed: Feb. 9, 2015

(65) Prior Publication Data
US 2015/0238154 A1   Aug. 27, 2015

(30) Foreign Application Priority Data
Feb. 26, 2014   (DE) .................. 10 2014 203 465

(51) Int. Cl.
   *A61B 6/03*   (2006.01)
   *G21K 3/00*   (2006.01)
   *A61B 6/00*   (2006.01)
   *A61B 6/06*   (2006.01)
   *A61B 6/04*   (2006.01)

(52) U.S. Cl.
   CPC ............ *A61B 6/4035* (2013.01); *A61B 6/032* (2013.01); *A61B 6/06* (2013.01); *A61B 6/467* (2013.01); *A61B 6/542* (2013.01); *A61B 6/544* (2013.01); *A61B 6/545* (2013.01); *A61B 6/0407* (2013.01)

(58) Field of Classification Search
   CPC .... A61B 6/032; A61B 6/4035; A61B 6/542; A61B 6/544; A61B 6/545
   USPC ............................................ 378/16, 156–159
   See application file for complete search history.

(56) References Cited

U.S. PATENT DOCUMENTS

| | | | | |
|---|---|---|---|---|
| 5,526,394 A * | 6/1996 | Siczek | ............... | A61B 6/4233 378/145 |
| 6,036,362 A * | 3/2000 | Schmitt | ............... | A61B 6/08 378/150 |
| 6,226,352 B1 * | 5/2001 | Salb | ............... | A61B 6/4035 378/143 |
| 6,597,758 B1 * | 7/2003 | Rosner | ............... | G01N 23/04 378/156 |
| 6,614,878 B2 * | 9/2003 | Bogatu | ............... | A61B 6/4042 378/156 |
| 6,633,627 B2 * | 10/2003 | Horiuchi | ............... | A61B 6/032 378/156 |

(Continued)

OTHER PUBLICATIONS

German Office Action dated Oct. 14, 2014 for corresponding German Application No. 102014203465.5.

*Primary Examiner* — Allen C. Ho
(74) *Attorney, Agent, or Firm* — Harness, Dickey & Pierce, P.L.C.

(57) ABSTRACT

A method is disclosed for selecting a radiation form, to change spatial distribution of the intensity and/or the spectrum of x-ray radiation of an x-ray source of an imaging system including a plurality of radiation form filters. The method includes acquiring a plurality of radiation absorption profiles of an examination object, of which image data is to be generated with the aid of the imaging system, in parallel with the patient axis from various directions; calculating an effective radiation absorption profile by averaging the recorded radiation absorption profiles; and selecting the radiation form filter on the basis of the effective radiation absorption profile of the examination object from a plurality of radiation form filters. An x-ray imaging system is further disclosed.

19 Claims, 2 Drawing Sheets

(56) References Cited

U.S. PATENT DOCUMENTS

| | | | | |
|---|---|---|---|---|
| 6,751,290 B2* | 6/2004 | Salb | A61B 6/4035 | 378/98.9 |
| 6,950,492 B2* | 9/2005 | Besson | A61B 6/508 | 378/16 |
| 6,968,030 B2* | 11/2005 | Hoffman | A61B 6/032 | 378/158 |
| 6,990,171 B2* | 1/2006 | Toth | A61B 6/032 | 378/158 |
| 7,046,756 B2* | 5/2006 | Hoffman | A61B 6/032 | 378/158 |
| 7,050,544 B2* | 5/2006 | Karlsson | A61B 6/502 | 378/148 |
| 7,068,750 B2* | 6/2006 | Toth | A61B 6/032 | 378/156 |
| 7,076,029 B2* | 7/2006 | Toth | A61B 6/032 | 378/158 |
| 7,092,490 B2* | 8/2006 | Saladin | A61B 6/4035 | 356/418 |
| 7,120,222 B2* | 10/2006 | Hoffman | A61B 6/032 | 378/124 |
| 7,313,217 B2* | 12/2007 | Toth | A61B 6/032 | 378/20 |
| 7,330,535 B2* | 2/2008 | Arenson | G21K 1/04 | 378/156 |
| 7,483,518 B2* | 1/2009 | Hamill | G21K 1/10 | 378/119 |
| 7,636,413 B2* | 12/2009 | Toth | A61B 6/032 | 378/157 |
| 7,649,981 B2* | 1/2010 | Seppi | A61B 6/032 | 378/124 |
| 7,653,179 B2* | 1/2010 | Ramsauer | A61B 6/06 | 378/157 |
| 7,680,249 B2* | 3/2010 | Yuan | A61B 6/00 | 378/156 |
| 7,695,193 B2* | 4/2010 | Flohr | A61K 49/04 | 378/207 |
| 7,715,522 B2* | 5/2010 | Goto | A61B 6/032 | 378/16 |
| 8,218,728 B2* | 7/2012 | Karch | A61B 6/032 | 378/156 |
| 8,218,731 B2* | 7/2012 | Gillett | G21K 1/043 | 378/158 |
| 8,284,903 B2* | 10/2012 | Yuan | A61B 6/06 | 378/156 |
| 8,571,178 B2* | 10/2013 | Sendai | A61B 6/4042 | 378/157 |
| 8,605,861 B2* | 12/2013 | Sipiorski | A61B 6/06 | 378/98.7 |
| 8,761,347 B2* | 6/2014 | Brown | A61N 5/1048 | 378/156 |
| 8,929,678 B2* | 1/2015 | Jvari | A61B 6/06 | 378/51 |
| 9,008,264 B2* | 4/2015 | Boone | A61B 6/583 | 378/207 |
| 9,254,109 B2* | 2/2016 | Becker | A61B 6/032 | |
| 2014/0005533 A1 | 1/2014 | Grasruck et al. | | |

* cited by examiner

METHOD FOR SELECTING A RADIATION FORM FILTER AND X-RAY IMAGING SYSTEM

PRIORITY STATEMENT

The present application hereby claims priority under 35 U.S.C. §119 to German patent application number DE 102014203465.5 filed Feb. 26, 2014, the entire contents of which are hereby incorporated herein by reference.

FIELD

At least one embodiment of the invention generally relates to a method for selecting a radiation form filter from a plurality of radiation form filters and/or to an x-ray imaging system having a selection unit for selecting a radiation form filter from a plurality of radiation form filters.

BACKGROUND

In the case of x-ray imaging systems, in particular in computed tomography systems, a diaphragm, which initially determines the opening angle of an x-ray beam bundle and the shape of a surface illuminated by the x-ray radiation, is usually attached between an x-ray source and the examination object. A radiation form filter is frequently arranged downstream of this diaphragm in the radiation path of the x-ray radiation, the radiation form filter also being able to change the intensity of the x-ray radiation both spatially or also spectrally. These are essentially planar filters, which are irradiated by the entire x-ray beam (typically delimited by the diaphragm), without the filter having in this way to comprise openings through which the x-ray radiation is able to pass unchanged. These filters are typically made of aluminum or Teflon.

In order to manipulate and further change the spectral or also spatial intensity distribution of the x-ray radiation, different types of radiation form filters, such as for instance bowtie filters (i.e. filters, which in addition focus or expand the x-ray radiation with convex or concave surfaces, typically similar to the shape of a bowtie) or also wedge-shaped filters, known as wedge filters, which can be introduced into the radiation path of the x-ray radiation between an x-ray source of the imaging system and an examination object individually or in combination with a number of radiation form filters. At least local extremes of the x-ray radiation intensity can be defined within the x-ray radiation bundle for instance with the aid of a bowtie filter. The intensity of x-ray radiation can be reduced by a continual attenuation value for instance with the aid of a wedge filter at right angles to the propagation direction of the x-ray radiation. The intensity minimum is usually at the periphery of a used x-ray radiation bundle (delimited by the diaphragm).

There is in particular the possibility of defining the size and/or extent of the irradiated region or regions of one or more radiation extremes. I.e. aside from different types of radiation form filters, there is also still the possibility of selecting between different radiation form filters of the same type. For instance, in the case of filters of the same type, it is possible to select between "narrow filters", which reduce the irradiated region spatially, or "wide filters" and "very wide" filters, which, if necessary, extend the irradiated region or the region of an intensity extreme.

Furthermore, it is likewise conceivable for the radiation form filter to spatially influence the spectrum of the used x-ray radiation in particular (i.e. when the filter is irradiated, the spectral intensity distribution of the x-ray radiation changes). For instance, in a spatial region determined by the filter, the spectrum of the x-ray radiation can be hardened, i.e. an intensity maximum of the x-ray radiation is changed to smaller wavelengths. Similarly, if necessary, the spectrum of the x-ray radiation can be adjusted more softly in the predetermined spatial region with the aid of the filter (i.e. an intensity maximum is changed to larger wavelengths).

The operator of an x-ray imaging system undertaking an x-ray recording thus has the choice between a plurality of filters, in order to optimize an x-ray recording. The optimization can on the one hand consist in ensuring the image quality of a provided recording and on the other hand also in keeping the radiation exposure of an examination object, on account of image acquisition, as low as possible. A corresponding optimization is based here largely on the experience of the operator.

Ideally, a suitable scan or examination protocol (i.e. a sequence of control steps) is stored for each application of the imaging system with respect to these optimization objectives, on the basis of which scan or examination protocol the image acquisition is controlled in the imaging system and which if necessary prespecifies a radiation form filter to be used. If there is no scan protocol available for a relevant application, this must firstly be generated based on the specialist knowledge of the operator. An optimal selection of the radiation form filters is in this case possibly not always ensured. Furthermore, the assignment of radiation form filters to specific protocols is complicated and stands in the way of a simplification of the operation of an x-ray imaging system.

In the case of an examination protocol for children, a radiation form filter is usually used. The radiation form filter could however also be used for adults as a function of the constitution of the patient and the scanning area, in order to reduce the x-ray dose. On the other hand, it may also be useful in certain instances, in the case of children, to omit the radiation form filter so as to achieve an improved image quality.

Radiation form filters were previously only used in protocols for children. Particularly narrow radiation form filters are usually used for children. In the case of adults, no radiation form filters are by contrast usually used. If a tall child now has the dimensions of an adult for instance, it may be meaningful to omit the radiation form filter or to use a wider radiation form filter, i.e. a radiation form filter with a wider irradiation range, for which no special protocol for children is provided. Nevertheless, in the case of the conventional method, in which special protocols, for instance for children, are assigned to the individual filters, the specific parameters specified in the protocols for children also got lost here. For instance, if instead for instance the radiation filter was omitted in the case of a child and a protocol for adults, in which a higher radiation dose is allowed, were accordingly to be used, a child could as a result be exposed to an excessively high radiation dose. Conversely, it may be meaningful for instance in the case of a small adult to use a radiation form filter. Nevertheless, no adult protocols are suited to the radiation form filters. If a special protocol for children, which is assigned to the radiation form filter used, is now used for adults, the result is not optimal. For instance, on account of an excessively low x-ray dose, the contrast is not as good as it could be in the best case, if an x-ray dose which is still acceptable for adults were to be used. There is therefore the problem that the protocols assigned to the filters or the protocols assigned to the recordings without filters are specified for specific age groups. If the filters or no filter were also to be used in the case of people in other age groups however, there is the problem of not being able to easily transfer the protocols for application on other age groups.

SUMMARY

At least one embodiment of the present invention improves x-ray recordings with respect to their quality or the radiation exposure of an examination object by way of the x-ray imaging, in particular when examining different age groups, or to enable a more flexible application of radiation absorption filters.

A method for selecting a radiation form filter and an x-ray imaging system are disclosed.

In accordance with at least one embodiment of the invention, an improved method for selecting a radiation form filter from a plurality of radiation form filters is proposed.

Furthermore, at least one embodiment of the inventive x-ray imaging system has a computing unit, which is set up to calculate an effective radiation absorption profile by averaging recorded radiation absorption profiles.

Further, particularly advantageous embodiments and developments of the invention result from the dependent claims and the subsequent description, wherein the independent claims of one claim category can also be further developed in a similar fashion to the dependent claims of another claim category.

BRIEF DESCRIPTION OF THE DRAWINGS

The invention is described below once again with reference to the accompanying figures based on example embodiments. Here the same components are provided with identical reference characters in the various figures, in which.

DETAILED DESCRIPTION OF THE EXAMPLE EMBODIMENTS

Figure 1:
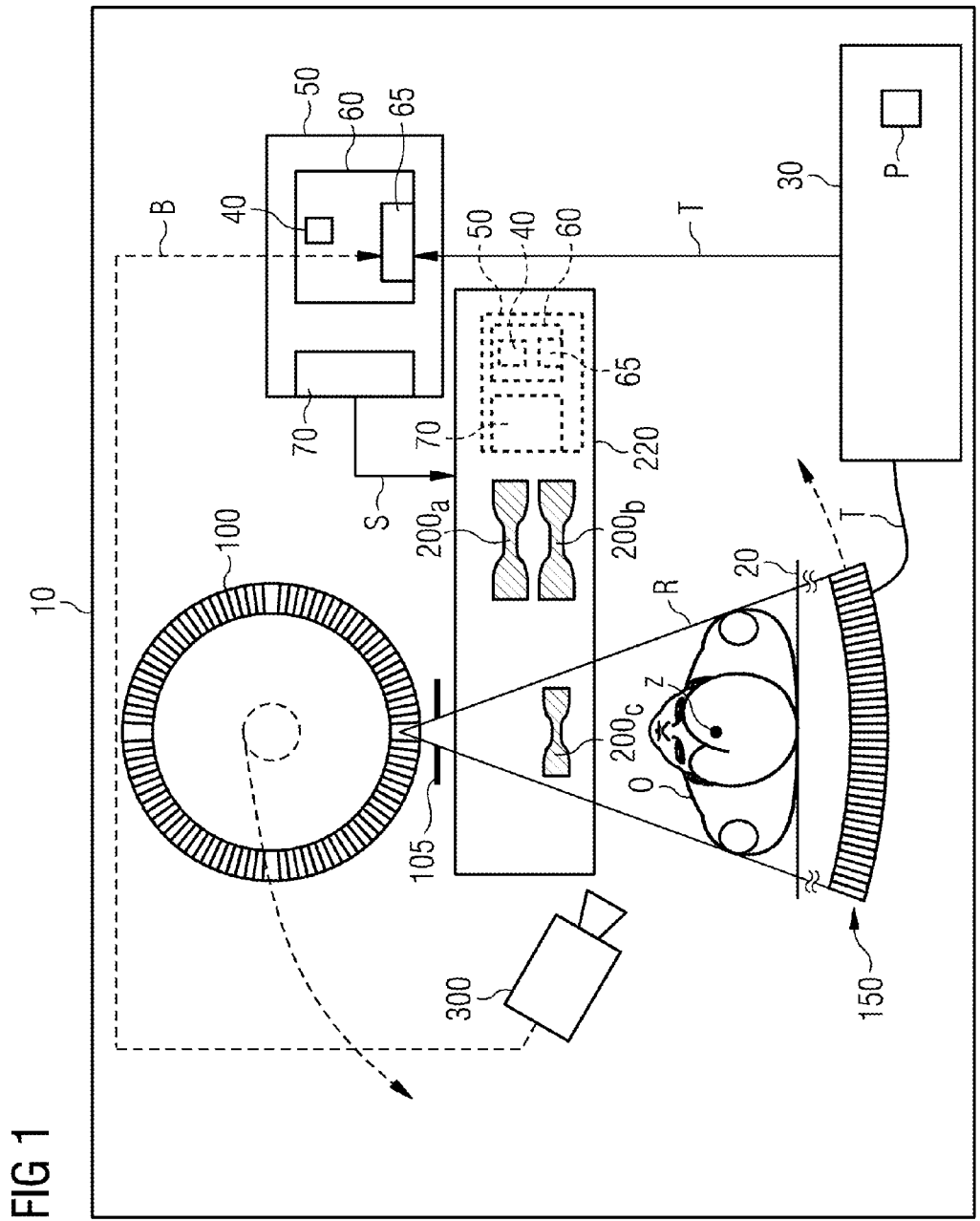
FIG. 1 shows a first example embodiment of an imaging system having an x-ray source and an x-ray detector, wherein a radiation form filter is automatically selected from a plurality of radiation form filters and is introduced into the radiation path of the x-ray source.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In accordance with at least one embodiment of the invention, an improved method for selecting a radiation form filter from a plurality of radiation form filters is proposed.

The radiation form filter, which can be embodied in particular as described in the introduction, in this way changes for instance the spatial distribution of the intensity and/or the spectrum of x-ray radiation of an x-ray source of an imaging system. The spectral change preferably likewise takes place spatially with respect to the wavelengths emitted by the x-ray source. The selection of a radiation form filter selection can also be understood as meaning that no radiation form filter is selected, in other words for instance the omission of a radiation form filter in a specific spatial region between the x-ray source and the examination object. In the following, a radiation form filter arrangement with a plurality of radiation form filters can also be understood as a radiation form filter.

According to at least one embodiment of the invention, a plurality of radiation absorption profiles of an examination object, of which image data is to be generated in a subsequent step with the aid of the imaging system, are acquired in parallel with the examination object axis from different directions.

According to at least one embodiment of the invention, anatomical data of a patient can be used for instance in particular from images, topograms and/or other images of the patient, in order to determine a radiation absorption profile.

In general terms, anatomical measurement data of an examination object is acquired by the absorption profiles, which examination object is to be scanned in a further step with the aid of the imaging system. Anatomical measurement data is understood to mean measurement data which is based on anatomical parameters such as for instance the shape, position or also structure of body parts, organs, tissue or cells. This means in particular that the anatomical measurement data directly or indirectly represents the cited anatomical parameters.

An effective radiation absorption profile is calculated from the recorded radiation absorption profiles by averaging the recorded radiation absorption profiles.

For instance, the absorption values of the effective radiation absorption profile can be calculated in the simplest case for instance in accordance with the following formula:

$$a_{\mathit{eff}}(x_i, y_i) = \overline{a}(x_i, y_i) = \frac{\sum_{k=1}^{K} a_k(x_i, y_i)}{K} \quad (1)$$

In this way K specifies the number of recorded radiation absorption profiles; $a_k(x_i,y_i)$ is the absorption value of the k-th recorded radiation absorption profile at the point $(x_i,y_i)$; $a_{\mathit{eff}}(x_i,y_i)$ is the absorption value of the determined effective radiation absorption profile at the point $(x_i,y_i)$.

In particular, with the aid of at least one embodiment of the inventive method, based on the effective radiation absorption profile and further anatomical measurement data, it is possible to determine which of the available radiation form filters is to be most advantageously selected for a planned x-ray scan.

According to an embodiment, a manual determination of a filter arrangement can be omitted by automatically determining or selecting a radiation form filter arrangement. A definitive confirmation step for selecting the filter arrangement can only be provided after the automatic determination.

In particular, at least one embodiment of the inventive selection may be independent of a measurement protocol for actuating the imaging system, which was mentioned at the start.

Alternatively, the imaging can also be controlled on the basis of a scan or examination protocol which is standardized with respect to the filter selection, for instance a protocol for a specific age group, so that the selection of an unsuitable radiation form filter can largely be ruled out. A step can then only be recorded for instance in this standardized measurement protocol for instance, in which the inventive determination or selection of a radiation form filter or a radiation form filter arrangement takes place automatically for instance. I.e. the actuation of the imaging system takes place on the basis of a measurement protocol, which includes the step of automatically selecting a radiation form filter or the determination of a radiation form filter arrangement using at least one embodiment of the inventive method. The standardized measurement protocol itself may have been created for instance with the aid of at least one embodiment of the inventive method.

In this case, it is also possible for instance to determine from the data obtained for the selection whether the person to be examined is a child or an adult and whether it may nevertheless be meaningful for instance, on account of the dimensions of the person to be examined for instance, in the case of an adult, to use a radiation form filter.

In at least one embodiment of the inventive method, in accordance with an embodiment, the selected radiation form filter arrangement can then be automatically introduced, in a further step, into the radiation path of the x-ray source of the imaging system.

It is preferred, as mentioned at the start, for the radiation form filter arrangement to be arranged downstream of a diaphragm of the x-ray imaging system in the radiation path of the x-ray radiation. In this way the radiation form filter arrangement is, as mentioned, advanced between the x-ray source and the examination object to be scanned, or radiation form filters are if necessary removed from the radiation path. This can take place for instance with the aid of a suitable robotic system, so that control instructions from the operator are also obsolete in this respect. The corresponding control steps may in turn be components of a suitable measurement protocol, which is then dynamically changed on the basis of the determined selection, in order for instance to implement the necessary control steps. Alternatively, the introduction of the determined radiation form filter arrangement into the radiation path of the x-ray radiation can also be a component of the automatic selection method, so that it is sufficient if the measurement protocol, as mentioned above, contains the step involving automatic selection of the radiation form filter.

In particular, at least one embodiment of the inventive method can be used in an x-ray imaging system, which has an acquisition unit for acquiring a plurality of radiation absorption profiles of an examination object, of which image data is to be generated in a subsequent step with the aid of the imaging system, in parallel with the patient axis from different directions.

The acquisition unit can also be embodied here as an interface, by way of which an anatomical parameter can for instance be directly acquired, if this is present for instance as a directly measured parameter value or also directly identifiable parameter. Furthermore, it is likewise conceivable for the acquisition unit to have the function of a parameter determination unit, which is embodied so as to generate or determine anatomical parameters or also parameter values, which are indirectly represented by the anatomical measurement data, from the anatomical measurement data.

Furthermore, at least one embodiment of the inventive x-ray imaging system has a computing unit, which is set up to calculate an effective radiation absorption profile by averaging recorded radiation absorption profiles.

In order to determine the suitable radiation absorption filter, at least one, and preferably even several radiation absorption profiles are therefore to be recorded, which can then be used in order to calculate the effective absorption profile. On the one hand, very precise information relating to the optimal radiation absorption filter can be obtained by averaging already fewer radiation absorption profiles. On the other hand, the use of a small number of radiation absorption profiles keeps the radiation exposure of the patient low for the acquisition of information for the filter selection.

Furthermore, at least one embodiment of the inventive x-ray imaging system has a selection unit for selecting a radiation form filter. In this way the selection unit is embodied to this end to select a radiation form filter from a plurality of radiation form filters on the basis of the effective radiation absorption profile of the examination object.

The selection can in addition also be carried out automatically on the basis of anatomical measurement data (or anatomical parameters determined therefrom).

Instead of an individual radiation form filter, a radiation form filter arrangement can also be selected or determined.

In particular, the selection unit can be combined with a filter determination unit. The filter determination unit firstly automatically determines one or more proposals to select a radiation form filter arrangement on the basis of the effective radiation absorption profile and for instance anatomical measurement data. The radiation form filter is then selected by the selection unit on the basis of the proposals determined by the filter determination unit. As mentioned, the selection unit can to this end be embodied for instance in order to acquire a confirmation of the user of the x-ray system, in order to implement a final selection of a radiation form filter or a radiation form filter arrangement for a planned x-ray measurement. It is conceivable for instance for the filter determination unit to be included in the selection unit or to be constructed separately from the selection unit.

Further, particularly advantageous embodiments and developments of the invention result from the dependent claims and the subsequent description, wherein the independent claims of one claim category can also be further developed in a similar fashion to the dependent claims of another claim category.

According to a simple embodiment of the method to be realized, the plurality of radiation absorption profiles can be recorded from the anterior-posterior direction and the lateral direction.

In concrete terms, two radiation absorption profiles can therefore be recorded for instance, one in the anterior-posterior direction and one in the lateral direction. This can be particularly meaningful if the object to be examined is aligned in parallel or perpendicular to the said directions, since the maximum and minimum dimensions are then included in the calculation of the effective absorption profile.

In a particularly preferred embodiment of the method, a patient-specific control protocol is selected independently of the selection of the radiation form filter, taking into account the radiation absorption profile and/or further measurement data. In this development, the selection of the filter is not only separated from the use of a specific control protocol, but in addition also performs the selection of the control profile with the aid of the recorded measurement data or the radiation absorption profile. For instance, it is possible to determine with the aid of the recorded measurement data, whether a protocol which is specific to children or an adult-specific protocol is to be applied. A still further automation of the imaging process can thus be achieved. As a result, the imaging methods can also be implemented by less qualified persons.

In order to achieve as realistic data as possible for the radiation absorption profile, it may be meaningful to record the plurality of radiation absorption profiles with the aid of x-rays.

If the radiation exposure of the patient is to be minimized, it may be meaningful to realize the acquisition of the data for the radiation absorption profiles by determining the patient contours without applying x-ray radiation. For instance, the patient contours can be measured with the aid of a camera.

As already mentioned, the recording of the radiation absorption profiles can also be implemented by taking additional information into account relating to the object to be examined. In more precise terms, a weighting of the recorded absorption profiles or also in the case of an indirect recording of the absorption profiles, for instance by a camera recording, additional data relating to the person to be examined or the body part or organ to be examined can for instance be included in the determination of the radiation absorption profiles or in the calculation of the effective radiation absorption profile. The mentioned additional information may relate for instance to the age, weight, size, body mass index and body region to be examined of the object to be examined or the person to be examined.

If a restricted region of the body is of particular interest, it may be meaningful for the averaging of the recorded radiation absorption profiles to have the additional weighting of a specific body region of the object to be examined. If, when applying the method, a specific organ is to be viewed particularly clearly on the recordings, a particularly strong weighting of a region taken up by this organ on the radiation absorption profiles is to be performed in the step of averaging the radiation absorption profiles and calculating an effective radiation absorption profile.

With a different weighting of individual recording regions of the radiation absorption profiles, the effective radiation absorption profile may result as follows for instance:

$$a_{\it{eff}}(x_i, y_i) = \overline{a}(x_i, y_i) = \frac{\sum_{k=1}^{K} g_k(x_i, y_i) \cdot a_k(x_i, y_i)}{K} \quad (2)$$

Here K is the number of recorded radiation absorption profiles; $g_k(x_i,y_i)$ is the weighting factor of the k-th recorded radiation absorption profile at the point $(x_i,y_i)$, where $$\frac{\sum_{k=1}^{K} g_k(x_i, y_i)}{K} = 1$$

is standardized; $a_k(x_i,y_i)$ is the absorption value of the k-th recorded radiation absorption profile at the point $(x_i,y_i)$; $a_{\it{eff}}(x_i,y_i)$ is the absorption value of the determined effective radiation absorption profile at the point $(x_i,y_i)$.

If a specific region, for instance a specific organ, is to be recorded for instance, this region can be easily more significantly weighted when determining the effective radiation absorption profile.

On the other hand, if as low a radiation exposure as possible is required, a type of worst case scenario can be assumed for instance, wherein the determination of the effective radiation absorption profile includes the recording of the widest profile across the scanning region as an effective radiation absorption profile.

The selection of the radiation form filter on the basis of the effective radiation absorption profile of the examination object can finally be realized for instance such that the selection is performed from the N present radiation form filters with the aid of the individual radiation absorption profiles of the radiation form filter. Previously determined radiation absorption profiles can therefore already be assigned to the already existing radiation form filters which are available for selection. When selecting the optimal radiation form filter with the aid of the individual radiation absorption profiles assigned in advance to the respective radiation form filters, only the individual radiation absorption profiles of the N radiation form filters need therefore be aligned with the determined effective radiation absorption profile. The radiation form filter of the N radiation form filters can then be selected with the radiation absorption profile which is best suited to the determined effective radiation absorption profile of the examination object.

The determination of the radiation form filter from the N radiation form filters with the radiation absorption profile which is best suited to the effective radiation absorption profile can include in particular the application of a differential measurement method. For instance, the least-squares method can be used as a differential measurement method.

The method can, if the least-error-squares method is applied, be implemented according to the following formula $$n_{opt} = \min(F(n)) = \min\left(\sum_{x_i, y_i} (a_{eff}(x_i, y_i) + a_n(x_i, y_i) - \overline{b_n})^2\right) \quad (3)$$

In this way $1<=n<=N$; N specifies the number of radiation form filters available for selection; $n_{opt}$ is assigned to the optimal radiation form filter; the coordinates $x_i$ and $y_i$ are coordinates of the absorption values of the effective radiation absorption profile at the point $(x_i,y_i)$; $a_{eff}(x_i,y_i)$ is the absorption value of the determined effective radiation absorption profile at the point $(x_i,y_i)$; $a_n(x_i,y_i)$ is, in this case, the absorption value of the radiation absorption profile of the n-th radiation form filter of the N radiation form filters which are available;

$$\overline{b_n} = \frac{\sum_{i=1}^{I} a_{eff}(x_i, y_i) + a_n(x_i, y_i)}{I}$$

is the average value of the added radiation absorption profiles of the patient and of the n-th radiation form filter; I is the overall number of pixels $(x_i,y_i)$. The calculation of the average value can possibly also include an additional weighting factor.

As mentioned, a selected radiation form filter arrangement, i.e. in particular also an individual radiation form filter, can be automatically introduced into or removed from the radiation path of the x-ray source in the inventive method for instance. This can take place for instance with a radiation form filter facility, which has an actuation unit or is connected to an actuation unit. The radiation form filter facility is then embodied so as to automatically introduce, during operation, a selected radiation form filter into the radiation path of the x-ray source or to remove the same from the radiation path. The radiation form filter facility to this end has for instance a robotic system, i.e. in particular an automatic drive, which can be based for instance on spring force, electrical energy, pneumatic or also hydraulic energy. The robotic system or the radiation form filter facility may receive corresponding filter control signals, which control the movement of the radiation form filters in or also out of the radiation path of the x-ray source, from the said actuation unit.

The filter control signals are generated by the actuation unit on the basis of the determined or selected form filter arrangement. For instance, the actuation unit can be included in the selection unit. A possibility of automatically modifying a radiation form filter arrangement is thus provided in particular.

The association of the person with a certain age group can be inferred from the determined measurement data in one development of the method. For instance, an age determination can take place with the aid of the bone density and a corresponding protocol, corresponding to the respective age group, can automatically be taken as the basis.

The type of examination region, such as for instance a heart or an arm, can further also form a basis of the inventive selection or determination of the radiation form filters or the radiation form filter arrangement. In particular, the spatial position or also structural parameters, such as for instance the type of tissue, may contribute to this basis.

The examination region or also the dimensions of the examination object can preferably be automatically determined so that manual inputs with respect to this data can be omitted.

Furthermore, the selection or determination of the radiation form filter or the radiation form filter arrangement can for instance take place automatically on the basis of the expected attenuation of the x-ray radiation through the examination object to be scanned. For instance, the weight of the patient could be measured and his geometrical dimensions determined in order to determine an expected attenuation.

In particular, the expected attenuation of the x-ray radiation can herewith be automatically determined. It is possible here, by automatically weighing the patient and measuring the size of the patient, to derive the expected attenuation of the x-ray radiation and also vice versa.

In addition to the direct measurement of the expected attenuation of the x-ray radiation for instance by means of a topogram or radiation absorption profile, there is therefore the possibility of using the mentioned anatomical parameters such as for instance weight or size of the patient or other structural information in addition to determine the effective absorption profile.

The described anatomical measurement data such as weight, size and examination region can in this way be taken into account differently when determining the radiation form filter arrangement.

The selection of radiation form filters can be determined for instance for a recording of the heart or skull essentially through the examination region. The examination region, in this case, essentially determines the attenuation of the x-ray radiation to be expected and also the spectrum of the x-ray radiation to be used. For recordings of the skull, provision can rather be made for instance for softer x-ray radiation, i.e. the radiation form filter changes the x-ray radiation spectrum with respect to the spectrum generated by the radiation source, to a softer spectrum. The spatial distribution can for instance be selected such that the examination object or an (examination) region of the examination object receives a high dose and the rest of the patient receives a lower dose compared with the high dose.

For instance, with the step of averaging the radiation absorption spectra, this may mean that certain regions, which are to be irradiated with a high dose, are weighted particularly significantly.

Ultrasound scans, MRT scans or also other pre-information can also be used for instance in order to determine the radiation absorption profiles.

In particular, a low-radiation acquisition of the radiation absorption profiles can thus take place, with the aid of which the overall radiation exposure of a patient can be minimized with respect to a planned x-ray examination. This can take place for instance such that it is possible to dispense with generating a topogram on the basis of a recording with x-rays in order to select the optimal filter or to control the x-ray imaging system.

It is further possible here to integrate one or more of the described components, units or facilities, into one another in order to achieve an optimized structure of the x-ray imaging system and to simplify the consideration of the mentioned interactions.

FIG. 1 schematically shows a cross-sectional representation perpendicular to a system axis of an x-ray imaging system, here a CT system 10, for generating two-, three- or multi-dimensional computed tomography image data. The CT system 10 essentially consists here of a conventional scanner, in which, on a gantry, an x-ray detector 150 with an x-ray source 100 opposing the x-ray detector 150, circulates about a measuring space. This is indicated schematically by dotted lines with a final arrow. Disposed in front of the scanner is a patient positioning facility or a patient couch 20, the upper part of which, with an examination object O or patient O located thereupon, can be moved relative to the scanner in the direction of the system axis z, in order to move the patient O relative to the x-ray detector 150 through the measuring space. The system axis z herewith simultaneously forms a shared circumferential axis of the x-ray detector 150 and of the x-ray source 100. The scanner and the patient couch 20 are actuated by a control facility 30, from which control data is sent by way of a conventional interface, in order to actuate the CT system 10 in accordance with a predetermined measurement protocol P.

It should be noted that the methods described below can basically also be used on other CT systems, e.g. with a detector forming a complete ring. The methods can also further be used in another x-ray imaging system for instance.

The raw data acquired by the x-ray detector 150 (i.e. x-ray projection data) is transferred to a measurement data interface of the control facility 30. This raw data is then further processed in an image reconstruction facility realized in the control facility 30 in the form of software on a processor, said image reconstruction facility reconstructing image data from the raw data for instance.

The finished computed tomographic image data or volume image data generated and reconstructed on the basis of the raw data is then transferred to an image data interface, which stores the generated image data in a memory of the control facility 30 for instance or outputs it conventionally on a monitor of the control facility 30 or feeds the data, via an interface, into a network connected to the computed tomography system, for instance an archiving system (PACS) or radiological information system (RIS) or stores the same in mass storage devices present there or outputs corresponding images on printers connected there. The data can also be further processed in any other manner and then stored or output.

The raw data acquired may in particular also be so-called topogram data T, which, in the concrete instance, represents the data of the recorded radiation absorption profile.

Figure 2:
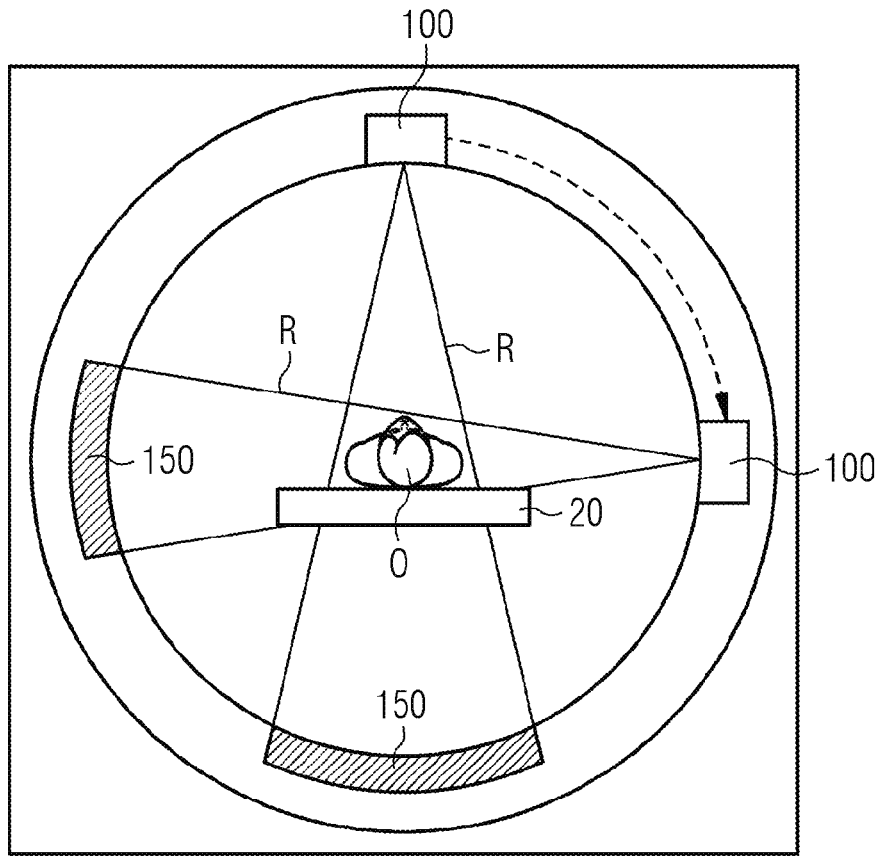
FIG. 2 shows the recording of a number of radiation absorption profiles in the anterior-posterior direction and in the lateral direction in accordance with an example embodiment of the invention.

FIG. 2 shows how topogram recordings or radiation absorption profiles T are recorded in the posterior-anterior direction, i.e. in the vertical direction and in the lateral direction. The patient O located on a patient couch 20 is irradiated by the x-ray source 100 once in the perpendicular direction and once in the vertical direction. The x-ray detector 150 is positioned here respectively at the point opposite the x-ray source 100. Two-dimensional projections are recorded as radiation absorption profiles T.

The recorded radiation absorption profiles T can be used, as explained in more detail below, within the scope of the invention, in order to select a radiation form filter or select a radiation form filter arrangement from a plurality of radiation form filters.

Different anatomical parameters can be inferred from the topogram data T, as explained above, directly and also indirectly. This takes place with the aid of an acquisition unit 65, which accepts the topogram data T and determines anatomical parameters therefrom. For instance topogram data T directly contains the attenuation of x-ray radiation R to be expected on account of the nature of the examination object O. The local attenuation to be expected at a specific detector position is in this case in particular dependent on anatomical parameters, such as for instance, the dimensions of the test subject O, i.e. in particular on the size, the weight, the position and structure of organs, body parts or tissues, so that these anatomical parameters can be determined or generated directly from the topogram data T. For instance, anatomical parameter values for the position, size or also structure of the head of the examination object can be obtained or generated from the topogram data T.

The position of an examination region can also be determined for instance on the basis of the topogram data T, in order for instance to targetedly enable the recording of the head, the heart or also the lungs.

Alternatively or in addition to the topogram data T, anatomical measurement data, from which anatomical parameters or parameter values can again be determined, can also be determined in the form of image data B, which is generated for instance by a camera 300. The represented camera 300 generates anatomical measurement data B in the form of scans or image data B of the patient O on the basis of light in the visible wavelength range, while the patient O is located on the patient couch 20. This scan can likewise be sufficient to generate parameters for the position, size or also structure of the head of the patient O.

In order to be able to determine the position of organs or other tissue, the image data B can be combined with pre-information, which can be provided for instance by ultrasound recordings or earlier MRT/CT recordings. It is also conceivable here for the ultrasound recordings to only be detected during or after the recording of the image data B and then to be combined for instance with the image data B or also topogram data T. The radiation exposure caused by the planned x-ray examination is not increased here, since this pre-information is already available and can be made available for instance as anatomical measurement data by way of the mentioned PACS system.

Furthermore, the weight of the patient O could for instance likewise be determined in advance or for instance with the aid of a weighing facility (i.e. based on a comparison of mass) or weighing mechanism (i.e. based on weight) of the patient couch 20 or also be estimated from image data B.

The thus available radiation absorption profiles T and further anatomical measurement data B, i.e. in particular the image data B, are then taken over by the acquisition unit 65, if necessary evaluated and transferred to a filter determination unit 60.

On the basis of the recorded radiation absorption profiles T and further determined anatomical measurement data B (or the thus associated anatomical parameters and/or parameter values), the optimal geometry of the x-ray radiation R emitted by the x-ray source 100 can be determined or selected. Similarly, this data determines the optimal wavelength spectrum of the x-ray radiation R. The filter determination unit 60 has a computer unit 40. This calculates, on the basis of the measured radiation absorption profiles, the effective radiation absorption profile T of the respective patient O.

The filter determination unit 60 determines herefrom and on the basis of the further anatomical parameters an optimal shape with respect to the spatial distribution of the x-ray radiation and of the spectrum of the x-ray radiation R used. This additional information influences the calculation of the effective radiation absorption profile by way of a weighting of the radiation absorption profiles T.

It may be meaningful for instance to use a radiation form filter for a CT recording of a heart, which, as mentioned at the start, is "narrower" than with abdomen or thorax recordings, in order for instance to direct the full x-ray intensity onto the examination region such as the heart for instance and to reduce the dose in the periphery. In this instance, the examination region significantly specifies for instance the geometric shape and also the spectral distribution of the x-ray radiation R which is optimal for the planned recording.

Furthermore, the size and fatness (or the weight) of the patient O can also significantly influence both the spectral distribution of the x-ray radiation R and also the geometric shape of the distribution of optimal x-ray radiation R. For instance, a "wider" radiation form filter, for obese patients O, can in turn be used compared with the standard filter provided for normal-weight patients for thorax recordings for instance. A hardened spectrum of the x-ray radiation would be used at the same time so that the optimal spectrum of the x-ray radiation R is also influenced by the size or the weight of the patient O.

Conversely, the parameters "size" or "fatness" can for children specify for instance the use of "narrower radiation form filters" with a "softer" spectrum of x-ray radiation R than with an adult patient.

At least one embodiment of the inventive method is now advantageous in that the cited details result directly from the recorded radiation absorption profiles T. The fatness of a person usually results for instance from the contours which can be identified on the radiation absorption profile T. On the other hand, the cited specific details can also be taken into account when recording the radiation absorption profiles T. Only a delimited region of the body can be irradiated for instance when recording the radiation absorption profiles T. Finally, the data acquired in addition to the radiation absorption profiles T can be used to weight the radiation absorption profiles T when calculating an effective radiation absorption profile.

According to an example embodiment of the invention, an optimal radiation form filter arrangement is determined by means of the filter determination unit 60 based on the existing radiation form filters 200a, 200b, 200c.

A selection unit 50 includes, in the example embodiment, aside from the mentioned acquisition unit 65, the filter determination unit 60, the computer unit 40 and an actuation unit 70, which, on the basis of radiation form filter arrangement determined with the aid of the filter determination unit 60, transfers filter control signals S to a radiation form filter facility 220. The selection unit 50 selects the determined radiation form filter 200c for a subsequently planned CT measurement.

The radiation form filter facility 220 has a robotic system, which, on the basis of the filter control signals S, introduces the selected radiation form filter 200c to a site in the radiation path of the x-ray radiation R which has been determined with the aid of the filter determination unit 60.

As indicated with a dashed line, the selection unit 50 may also form part of the radiation form filter facility 220. Furthermore, the selection unit 50 can be realized in another way, for instance at least partially in the form of software on a processor of the CT system 10 and in particular on a processor of the control facility 30.

In the example embodiment shown in FIG. 1, a bowtie filter 200c is introduced in the radiation path of the x-ray radiation R downstream of a diaphragm 105 between the x-ray source 100 and the patient O.

With the aid of the diaphragm 105, a bundle of x-ray radiation R which irradiates the patient O is initially defined. A fan or cone beam is in the customary manner delimited for instance with the aid of the diaphragm 105. The subsequently arranged bowtie filter 200c determines the spatial intensity of the x-ray radiation R such that maximum radiation intensity of the x-ray radiation R strikes the region of the heart of the patient O. The intensity distribution is set here along an axis, which runs perpendicular to the system axis z.

Figure 3:
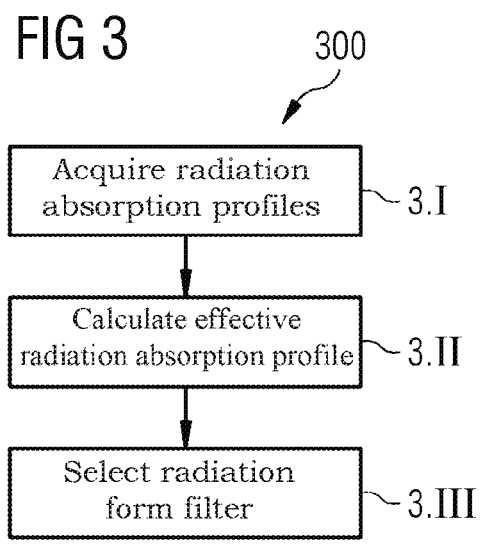
FIG. 3 shows a flow diagram, which clarifies the method according to an example embodiment of the invention.

FIG. 3 illustrates the method 300 for selecting a radiation form filter. In the step 3.I a plurality of radiation absorption profiles T of an examination object O, of which image data is to be generated in a subsequent step with the aid of the CT system 10, is acquired in parallel with the examination object axis z from different directions. In step 3.II, an effective radiation absorption profile or radiation absorption profile is calculated by averaging the recorded radiation absorption profiles and in step 3.III, the radiation form filter 200c is selected on the basis of the effective radiation absorption profile of the examination object O from a plurality of radiation form filters 200a, 200b, 200c. The selection between N radiation form filters with the aid of the individual radiation absorption profile of the radiation form filters can take place by aligning the previously assigned, individual radiation absorption profiles of the N radiation form filters with the effective radiation absorption profile of the examination object O and selecting the radiation form filter 200c of the N radiation form filters 200a, 200b, 200c with the radiation absorption profile which is best suited to the determined effective radiation absorption profile. For instance, a radiation form filter is particularly well suited to an effective radiation absorption profile of an examination object if the overall absorption of the radiation form filter and of the examination object O is constant or uniform across the irradiation surface or the radiation cross-section.

The selection of the radiation form filter from the N radiation form filters 200a, 200b, 200c may include in particular a differential measurement method. Here the least-square method is used to determine for instance which combination of the respective radiation form filter or the radiation absorption profile of the respective radiation form filter and the recorded or calculated effective radiation absorption profile of a patient for instance produces the most uniform radiation absorption profile.

The described method can preferably be implemented automatically. The faulty use of scan protocols is on the one hand prevented by the described method. A specific protocol suited for instance only to a special age group is then not necessarily assigned to the individual filters. Instead, the suitable filter can be selected independently of the age group. An optimal dose distribution with an optimized image quality can be achieved by the preferably automated selection of the optimal form filter. Contrary to the conventional method, an individual adjustment to the patient takes place. In addition, the process steps of the method can be processed easily and briefly.

Finally, particularly in the case of the automatic selection of the radiation absorption filter, no special knowledge is required from the operator or physician with respect to the creation of recording protocols, since the automatic selection of the suitable form filter does not require any specialist engagement or decision-making processes based on detailed specialist knowledge of the operating personnel.

In conclusion, reference is to be made to the fact that the features of all example embodiments or developments disclosed in figures can be used in any combination. In conclusion reference is likewise made to the fact that the x-ray imaging system described in detail above and the method for selecting a radiation form filter are merely example embodiments, which can be modified by the person skilled in the art in a variety of ways, without departing from the scope of the invention. Furthermore, the use of the indefinite article "a" or "an" does not rule out the possibility that relevant features may also be present several times. Similarly, the term "unit" does not rule out the possibility that relevant components consist of several interacting sub-components, which may if necessary also be distributed spatially.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for selecting a radiation form filter, to change spatial distribution of at least one of intensity and spectrum of x-ray radiation of an x-ray source of an imaging system, including a plurality of radiation form filters, the method comprising:
   acquiring a plurality of radiation absorption profiles of an examination object, from image data generated with the imaging system, in parallel with the axis of the examination object from various directions;
   calculating an effective radiation absorption profile by averaging the plurality of radiation absorption profiles; and
   selecting the radiation form filter, on the basis of the calculated effective radiation absorption profile, from a plurality of radiation form filters.

2. The method of claim 1, wherein the acquiring of the plurality of radiation absorption profiles of an examination object includes recording the plurality of radiation absorption profiles from the anterior-posterior direction and the lateral direction.

3. The method of claim 2, wherein the recording of the radiation absorption profiles comprises taking additional information into account relating to the examination object.

4. The method of claim 3, wherein the additional information includes at least one of age, weight, size, body mass index and body region to be examined of the examination object.

5. The method of claim 2, further comprising: selecting a patient-specific measurement protocol by taking at least one of the effective radiation absorption profile and further measurement data into account.

6. The method of claim 1, further comprising: selecting a patient-specific measurement protocol by taking at least one of the effective radiation absorption profile and further measurement data into account.

7. The method of claim 6, wherein the acquiring of the plurality of radiation absorption profiles of an examination object includes acquiring the plurality of radiation absorption profiles with x-rays.

8. The method of claim 6, wherein the acquiring of the plurality of radiation absorption profiles of an examination object includes taking additional information into account relating to the examination object.

9. The method of claim 8, wherein the additional information includes at least one of age, weight, size, body mass index and body region to be examined of the examination object.

10. The method of claim 1, wherein the acquiring of the plurality of radiation absorption profiles of an examination object includes acquiring the plurality of radiation absorption profiles with x-rays.

11. The method of claim 1, wherein the examination object is a patient and wherein the acquiring of the plurality of radiation absorption profiles of an examination object includes measuring contours of the patient.

12. The method of claim 11, wherein the measuring of the patient contours includes measuring contours of the patient with a camera.

13. The method of claim 1, wherein the averaging of the plurality of radiation absorption profiles comprises the weighting of a specific body region of the examination object.

14. The method of claim 1, wherein the selecting of the radiation form filter, on the basis of the effective radiation absorption profile of the examination object, includes selecting from a plurality of radiation form filters with individual radiation absorption profiles of the plurality of radiation form filters.

15. The method of claim 14, wherein the selecting of radiation form filter from a plurality of radiation form filters includes selecting the radiation form filter from the plurality of radiation form filters with the individual radiation absorption profile which is best suited to the effective radiation absorption profile of the examination object.

16. The method of claim 15, wherein the selecting of the radiation form filter from the plurality of radiation form filters includes applying a differential measurement method.

17. The method of claim 16, wherein the differential measurement method includes a least-square method.

18. An x-ray imaging system, comprising:
an x-ray source;
an acquisition unit to acquire a plurality of radiation absorption profiles of an examination object, from image data generated with the imaging system, in parallel with the axis of the examination object from various directions;
a computing unit, to calculate an effective radiation absorption profile by averaging the plurality of radiation absorption profiles of the examination object; and
a selection unit to select, on the basis of the calculated effective radiation absorption profile of the examination object, a radiation form filter from a plurality of radiation form filters.

19. The x-ray imaging system of claim 18, further comprising:
a radiation form filter facility, including a plurality of radiation form filters and an actuation unit, in order, during operation, to automatically bring a selected radiation form filter into the radiation path of the x-ray source.

* * * * *